(12) United States Patent
Naylor et al.

(10) Patent No.: US 6,246,902 B1
(45) Date of Patent: Jun. 12, 2001

(54) LEAD SET FILTER FOR A PATIENT MONITOR

(75) Inventors: Thomas Kipling Naylor, Belmont, MA (US); Clifford Kelly, Windham, NH (US); Scott W. Newell, Ipswich, MA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/304,378

(22) Filed: May 4, 1999

(51) Int. Cl.[7] .................................................. A61B 5/0402
(52) U.S. Cl. ........................................... 600/509; 128/901
(58) Field of Search ............................... 607/63; 600/509; 128/901

(56) References Cited

U.S. PATENT DOCUMENTS 5,217,010 * 6/1993 Tsitlik et al. .
6,063,234 * 5/2000 Chen et al. .......................... 156/345

* cited by examiner

*Primary Examiner*—Scott M. Getzow
(74) *Attorney, Agent, or Firm*—Alexander J. Burke

(57) ABSTRACT

A shielded conductor path comprising: a first signal conductor having an input end for acquiring a physiological signal and an output end for coupling the physiological signal to a physiological signal input of a patient monitor, and a second signal conductor positioned with respect to the first signal conductor for acting as a shield therefore. An inductance connected in series between an output end of the second signal conductor and the reference signal input of the patient monitor forms a filter circuit which attenuates the level of an interference signal in the second signal conductor. In one preferred embodiment of the invention, the inductance is part of an RLC filter circuit contained in a housing which is selectively insertable between an EKG lead set and the EKG signal input of a patient monitor. The selectively insertable filter permits the use of standard EKG lead sets in the presence of RF electrosurgery procedures, without risk of burning the patient at the site of the EKG electrodes.

11 Claims, 1 Drawing Sheet

LEAD SET FILTER FOR A PATIENT MONITOR

BACKGROUND OF THE INVENTION

1. Field of the Invention

The invention relates to physiological signal monitoring systems, and more particularly to an interference filter for connection to or incorporation with a lead set supplying physiological signals to a patient monitor.

2. Description of the Prior Art

It is standard practice to monitor the heart (EKG) and other physiological signals of a patient during a medical procedure. Surgical procedures typically use an electrocautery device in which a surgical knife is supplied with a relatively high level of radio frequency (RF) current so that blood vessels and other tissues are cauterized and sealed immediately upon cutting. However the presence of such high level RF signals and energy on the body of the patient, and particularly in the region of the sensors used to acquire EKG signals, can cause severe electro-surgical interference (ESI) which can easily disrupt the operation of the patient monitor and cause a burning of the patient at the sensor site. High level RF interference signals can also come from other sources, such as the pulsed RF signals used during a magnetic resonance imaging procedure. Typically, if no precautions are taken, such high level RF signals will damage the sensitive input circuits of the patient monitor, and at the very least, so disrupt the input circuits as to cause them to overload and prevent monitoring of the physiological signals of the patient for many seconds. Such disruption in patient monitoring is highly undesirable.

Accordingly, the prior art has addressed the following issues during Patient monitor design:

1. The shielded lead wires which connect a plurality of patient mounted EKG electrodes to the patient monitor unwittingly provide a conduction path for these RF interference currents. If the RF current picked up by the electrodes is high enough, the skin may be burned at the electrode sites. The current path is from one electrode wire through its cable capacitance to its shield and back through the shield capacitance of another electrode cable to the electrode wire for that other electrode. (This assumes, as is typically the case, that the shields for all electrode wires are connected together at some point in the conduction path leading up to the signal processing circuits at the front end of the patient monitor.)

This potential hazard is typically prevented in the prior art by designing special electrode sets having high impedance elements such as inductors and/or resistors in series with the signal conductor connected to each electrode, such as at the contact point or "grabber" of the EKG electrode. U.S. Pat. No. 4,951,672 is typical thereof, and has series connected resistors in the lead wire sets for reducing the RF signals caused during magnetic resonance imaging. Such special electrode sets are typically only used in such limited and specialized situations because the high impedance elements may not be compatible with the monitoring of other physiological signals of the patient, such as respiration monitoring which applies a low level current to the patient via the EKG electrodes, and determines respiration using impedance techniques. On the other hand, U.S. Pat. No. 4,800,894 is representative of another prior art solution which simply avoids this problem completely, by using, for example, a "time out" circuit connected between the EKG electrode lead wire set and the signal input to the patient monitor. The time-out circuit literally removes all signal from the patient monitor signal inputs during the detected presence of RF interference.

2. If EKG signals of the patient are to be monitored during such procedures, the RF interference voltages at the patient mounted electrodes must be filtered. Typically, averaging filters are effective at removing such RF interference signals. Furthermore, such as shown by U.S. Pat. No. 4,245,649, the patient monitor input circuits which amplify the EKG signals typically use voltage clamps for protecting the input circuits from excessive voltages, such as those generated by a defibrillator. However, if the RF interference voltages at the electrodes is high enough, the action of the averaging filter will not provide a sufficient reduction in the level of the interference signal and the voltage clamps will conduct, causing rectification and subsequent translation of the RF signals to lower "in band" signal frequencies. Such frequency translation typically causes interference with proper monitoring of the EKG and other physiological signal.

A combination of filtering inside the patient monitor and the high impedance elements in the electrode lead wire or the lead wire grabbers have also been used to filter the RF interference voltage and to reduce the amplitude of the voltage below the clamping voltage of the amplifier protection circuits. However, effectively filtering such voltage to prevent the clamps from operating in the impedance respiration circuits is problematic because the respiration circuits may operate at a frequency which is close to that of the RF interference signal, e.g., the frequency of the electrosurgical RF signal. Furthermore, as noted above, the respiration circuit of the monitor typically can't tolerate a high impedance in series with the electrodes because the impedance changes experienced during . respiration monitoring are very low.

It would be desirable to provide a more effective and versatile RF interference filter arrangement for a patient monitoring system.

SUMMARY OF THE INVENTION

A shielded conductor path for coupling physiological signals acquired from a patient to a patient monitor, in the presence of an interference signal acquired by the shielded conductor path. The shielded conductor path includes a first signal conductor having an input end for acquiring a physiological signal and having an output end adapted for coupling the physiological signal to a physiological signal input of a patient monitor, and a second signal conductor positioned with respect to the first signal conductor for acting as a shield therefor. The second signal conductor has an output end adapted for being coupled to a reference point associated with the physiological signal input of the patient monitor. An inductance is connected in series between the output end of the second signal conductor and the reference point of the patient monitor for forming a filter circuit which attenuates the level of the interference signal in the second signal conductor.

DETAILED DESCRIPTION OF THE INVENTION

Figure 1:
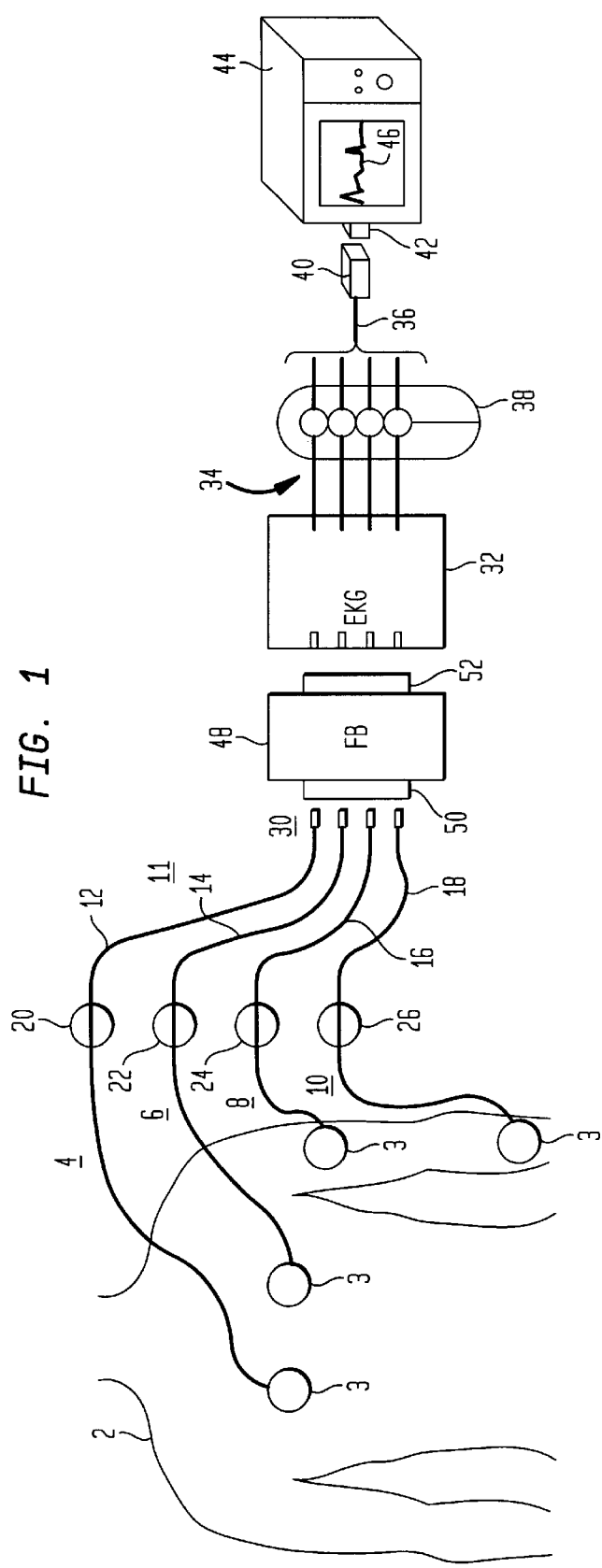
FIG. 1 illustrates a lead wire assembly constructed in accordance with the principles of the present invention, used with a patient monitor system.

Reference is now made to FIG. 1, which illustrates a lead wire assembly constructed in accordance with the principles of the present invention, used in a patient monitor system.

A patient 2 has a plurality of physiological sensors 3, e.g., EKG sensors, mounted on her body. A corresponding plurality of shielded lead wires 4, 6, 8 and 10, commonly referred to as a lead wire set 11, have one end of each of their respective signal conductors 12, 14, 16 and 18 connected to a respective one of the EKG sensors, for picking up or sensing heart (EKG) signals of the patient, and terminate at a pin connection in an respective one of connectors 30 (the pin connection not being specifically shown). Each of the EKG signal conductors 12, 14, 16 and 18 includes an associated one of shields 20, 22, 24, and 26 which act as an interference frequency signal shield for its respective signal conductor, each shield also having at a connection in a respective one of connectors 30 (details of the connection are a design choice and are therefore not specifically shown).

In accordance with prior art techniques, connectors 30 were normally inserted directly into an EKG pod 32 (also called an EKG intermediate cable or junction box 32), wherein defibrillation protection circuitry, typically using passive elements, was provided. The individual EKG signals are output from pod 32 on individual shielded cables 34, physically grouped together to form a single cable 36 having a common shield 38 connected to the shields of the individually shielded cables 34. Cable 36 terminates at a multi-pin connector 40 which is then inserted into a mating connector 42 of a patient monitor 44. Mating connectors 40/42 provide individual connections for the conductors carrying the EKG signals, and provides a common connection for shield 38 to a shield and patient connected reference point or ground for the patient monitor and its EKG signal processing circuits, not specifically shown. Monitor 44 processes the EKG signals applied to its signal input connector 42 in a conventional manner, for displaying at least one waveform 46 representative thereof.

In accordance with the principles of the present invention, an interference frequency filter unit 48 is provided. In one preferred embodiment of the invention, filter unit 48 includes a set of input connectors 50 and output connectors 52 for facilitating its connection between the connectors 30 of lead wire set 11 and the input side of EKG junction box 32. In an alternative embodiment of the invention, to be described more later on, filter unit 48 can be included at the signal input of monitor 44 or even "built-in" to monitor 44.

Filter unit 48 aids the interference filters which are internal to monitor 44 so as to prevent, for example, the voltage clamps associated with its EKG amplifier and impedance respiration circuits from operating. Overall, this results in a much improved interference rejection performance for the monitor system.

Figure 2:
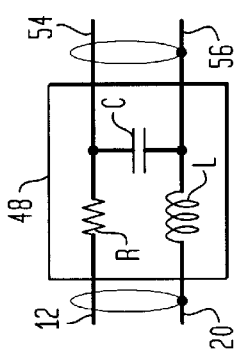
FIG. 2 illustrates details of a portion of the lead wire assembly shown in FIG. 1.

Filter unit 48, shown in detail in FIG. 2, comprises identical filter components for each of the individually shielded lead wires 4, 6, 8 and 10. Accordingly, filter components for only a representative shielded lead wire 4 of lead wire set 11 is shown. A resistance R, illustrated as a resistor, which can withstand the high voltage and high energy of defibrillation signals, is connected in series with conductor 12 of lead wire 4. In the illustrated embodiment a value of 10 K ohm is used for resistor R. Next, an inductance L, illustrated as an inductor, is connected in series with shield 20. Finally, a capacitance C, illustrated as a capacitor, is used to connect the output ends of filter unit 48 together, i.e., for bridging signal conductor 54 to its shield conductor 56. In the illustrated embodiment a value of 3.3 nanofarads is used for the capacitor C. In operation, filter unit 48 limits the coupling of the interference signal currents back to electrodes 3 via the shields of the shielded cables of lead wire set 11 by attenuating the interference signal. In the illustrated embodiment a value of 6.8 mH is used for the inductor L.

In accordance with prior art techniques, the inductors which formed the interference signal filters were connected in series with the electrode "grabbers", i.e., in series with the EKG signal conductors. Unfortunately, this prior art technique prevents the lead wire set from being used if it is also desired to provide impedance respiration monitoring. In the design of the present invention, the inductors are connected in series with the shields of the signal conductors, and in one preferred embodiment of the invention are housed in a separate unit which includes input and output connectors 50 and 52 for allowing filter unit 48 to be selectively coupled between the output connections 30 of lead wire set 11 and the input connections of EKG junction box 32. Use of a separate filter block 48 allows use of standard electrode cable sets, and permits impedance respiration operation when the filter unit 48 is selectively removed. Note, although this circuit placement of the inductors renders the shields less effective at high frequencies, the inductors are a low impedance for frequencies within the signal bandwidth of the EKG or other physiological signals.

Another important advantage of the illustrated preferred embodiment of the invention is the use of an RLC filter. The RC part of the filter can provide the electrosurgery filtering for the EKG amplifiers at a corner frequency of approximately 5 kHz. An LC filter for this purpose would be impractical due to the limited capacitive loading permissible on the electrodes and the limits of inductor size.

In the present invention the inductance limits the high frequency currents coupled to the shields of the electrode cables and the resistance provides for damping of the LC filter. If the LC filter is not adequately damped, the electrosurgery voltage may be amplified at frequencies near the resonant frequency of the LC filter. It is also important to match the values of the resistance and capacitive components to minimize common mode to differential conversion of the interference signals.

An additional advantage of the present invention is that the inductors don't have to withstand the higher currents present during defibrillation, which they would be subjected to if they were positioned in accordance with prior art techniques to be in series with the electrode conductors.

As noted above, in operation filter 48 permits the use of standard electrode lead sets during electrosurgery. When using transportable monitors which travel with the patient to different areas of the hospital, such as into and out of the operating room, this feature is particularly advantageous because the standard electrode lead set (typically comprising 3 to 6 individual EKG electrode connections to the patient), does not have to be disturbed, and only a single cable is needed to be unplugged to install the filter. This advantage is particularly important to the patient care providers since the electrodes are connected to the body of the patient while the intermediate block, EKG pod 32, is normally clipped to the bed sheet where it is more easily accessible to the care providers.

Figure 3:
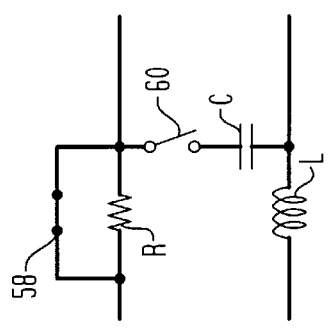
FIG. 3 illustrates details of an alternative embodiment of the portion of the lead wire assembly shown in FIG. 2.

Thus, there has been shown and described a novel method and apparatus for reducing the level of an interference signal in a lead wire associated with a patient monitor. Many changes, modifications, variations and other uses and applications of the subject invention will, however, become apparent to those skilled in the art after considering this specification and its accompanying drawings, which disclose a preferred embodiment thereof. For example, although the components of filter 49 are shown as lumped elements, they could in fact be distributed impedance's, or even active elements. The important aspect is that the effective RLC values reside in the places previously described. Additionally, an RL filter, instead of an RLC filter, may be sufficient for a given application. Furthermore, it should be noted that once the lead wire conductors for the shield are coupled to the patient monitor, they may be connected to a system or local ground (or other reference point), without altering their function as a shield. Furthermore, although the components of filter 48 are preferably located in a separate housing to facilitate the use of standard lead wire sets, and easy removal of filter 48 from the signal path to monitor 44, such components can also be "built-into" monitor 44. In the event that filter 48 is not easily removable from lead wire set 11 or the input circuits of monitor 44, filter 48 could be modified, as shown in FIG. 3, to include a switching arrangement comprising a first switch 58 for selectively bridging the resistor R, and a second switch 60 for selectively disconnecting the capacitor C. In operation, when the switch 58 is open, switch 60 is closed, for causing the RLC filter circuit to operate so as to attenuate the interference signal. Conversely, when switch 58 is closed, switch 60 is open, for bypassing the operation of the RLC filter circuit.

All such changes, modifications, variations and other uses and applications which do not depart from the teachings herein are deemed to be covered by this patent, which is limited only by the claim which follow as interpreted in light of the foregoing description.

What is claimed is:

1. An apparatus for coupling physiological signals acquired from a patient to a physiological signal processing circuit in a patient monitor, in the presence of an interference signal acquired by the apparatus, said apparatus comprising:

a first signal conductor having an input end adapted for coupling to a physiological signal sensor coupled to a medical patient for acquiring a physiological signal, and having an output end adapted for coupling the physiological signal to a physiological signal input of a physiological signal processing circuit in a patient monitor;

a second signal conductor positioned for shielding the first signal conductor from the input end to the output end, the second signal conductor having an output end adapted for coupling to a reference point associated with the physiological signal processing circuit of the patient monitor; and a first inductance connected in series with the second signal conductor for forming a filter circuit which attenuates the level of the interference signal in the second signal conductor, wherein there is no series coupled inductance in the first conductor corresponding to the first inductance in the second conductor.

2. The apparatus of claim 1, comprising a plurality of shielded conductor paths, with the first signal conductor of each path adapted to be coupled to a physiological signal sensor mounted on a patient, and an inductance connected in series between the output end of each of the second signal conductors and associated reference point inputs of the patient monitor for forming a plurality of filter circuits, each filter circuit for attenuating the level of the interference signal in a respective one of the shielded conductor paths.

3. The apparatus of claim 1, further including: a switching arrangement coupled to the inductance for selectively removing the attenuating effect of the filter circuit on the interference signal.

4. The apparatus of claim 1, wherein the inductance is part of an RLC filter, comprising:

a resistance connected in series between the output end of the first signal conductor and the physiological signal input of the patient monitor, and a capacitance for bridging the first and second signal conductors at the point between the series connections of both of the resistance and inductance to the patient monitor.

5. The apparatus of claim 4, further including:

a switching arrangement coupled to the RLC filter for selectively removing the attenuating effect of the filter circuit on the interference signal.

6. The apparatus of claim 5, wherein the switching arrangement comprises a first switch for selectively bridging the resistance, and a second switch for selectively disconnecting the capacitance, the first switch being open and second switch being closed for causing said RLC filter circuit to operate so as to attenuate the interference signal.

7. The apparatus of claim 1, wherein the inductance is located in a housing adapted for being selectively coupled between the output end of the second signal conductor and the associated reference point input of the patient monitor.

8. The apparatus of claim 2, wherein the inductance is located in a housing adapted for being selectively coupled between the output end of the second signal conductor of each of the plurality of shielded conductor paths, and reference signal inputs of the patient monitor.

9. The apparatus of claim 8, wherein the housing is adapted for being selectively coupled between an EKG lead wire set adapted for being coupled to a plurality of EKG signal sensors mounted on the medical patient, and EKG signal inputs of a patient monitor.

10. The apparatus of claim 8, wherein the housing includes a switch arrangement in the leadwire set for selectively removing the attenuating effect of the filter circuit on the interference signal.

11. A conductor path for coupling a physiological signal acquired from a patient to a physiological signal processing circuit in a patient monitor, in the presence of an interference signal acquired by the conductor path, said conductor path comprising:

a first signal conductor path having an input end adapted for coupling to a physiological signal sensor coupled to a medical patient for acquiring a physiological signal, and having an output end adapted for coupling the physiological signal to a physiological signal input of a physiological signal processing circuit in a patient monitor;

a second signal conductor positioned for shielding the first signal conductor from the input end to the output end, said second signal conductor having an output end adapted for coupling to a reference point associated with the physiological signal processing circuit of the patient monitor; and a first inductance coupled in series with the second signal conductor wherein there is an absence of a series coupled inductance in the first conductor corresponding to the first inductance in the second conductor.

* * * * *